US007445908B2

(12) United States Patent
Paul (10) Patent No.: US 7,445,908 B2
(45) Date of Patent: Nov. 4, 2008

(54) DETECTION OF OXIDIZING AGENTS IN URINE

(75) Inventor: Buddha D. Paul, Germantown, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 839 days.

(21) Appl. No.: 10/827,282

(22) Filed: Apr. 20, 2004

(65) Prior Publication Data

US 2004/0259186 A1 Dec. 23, 2004

Related U.S. Application Data

(60) Provisional application No. 60/479,187, filed on Jun. 18, 2003, provisional application No. 60/529,700, filed on Dec. 16, 2003.

(51) Int. Cl.
*C12Q 1/26* (2006.01)
(52) U.S. Cl. .............................. 435/25; 435/10; 435/12; 435/25; 436/73; 436/74; 436/84
(58) Field of Classification Search ................ 436/73, 436/74, 84; 435/10, 12, 25–28
See application file for complete search history.

(56) References Cited

U.S. PATENT DOCUMENTS

| 4,558,100 | A | * | 12/1985 | Kightlinger et al. ...... 525/329.1 |
| 5,151,370 | A | * | 9/1992 | Denney ........................ 436/74 |
| 5,219,760 | A | * | 6/1993 | Herrmann et al. ............. 436/84 |
| 5,264,348 | A | * | 11/1993 | Schick et al. ................. 435/28 |
| 5,552,268 | A | * | 9/1996 | Herbert et al. ................. 435/4 |
| 5,804,404 | A | * | 9/1998 | Heras et al. ................... 435/28 |

(Continued)

FOREIGN PATENT DOCUMENTS

WO    WO 90/02339    *    3/1990

OTHER PUBLICATIONS

Banerjee, Dibyajyoti, "Urinary Hydrogen Peroxide: A Probable Marker of Oxidative Stress in Malignancy", 2003, Elsevier, 334, 205-209.*

(Continued)

*Primary Examiner*—Jill Warden
*Assistant Examiner*—Imran Akram
(74) *Attorney, Agent, or Firm*—Elizabeth Arwine (57) ABSTRACT

A method of detecting oxidants in a biological sample comprising: adding a source of ferrous ions to said sample, whereby the presence of oxidants in said sample oxidize at least a portion of said ferrous ions to ferric ions; adding a chromogenic compound to said sample, whereby said chromogenic compound reacts with at least a portion of any ferric ions present in said sample; and detecting for the product of said chromogenic compound-ferric ion reaction; whereby the detection of said chromogenic compound-ferric ion reaction product indicates the presence of oxidants in said sample. The method of detecting adulteration of a urine sample also comprises adding a source of ferrous ions to a urine sample; adding a chromogenic compound to said urine sample; detecting the presence or absence of a chromogenic reaction product; determining a concentration of said chromogenic reaction product; and determining if said concentration signifies adulteration of said urine sample.

28 Claims, 3 Drawing Sheets

U.S. PATENT DOCUMENTS

| | | | |
|---|---|---|---|
| 6,177,260 B1 * | 1/2001 | Benzie et al. | 435/25 |
| 6,468,805 B1 | 10/2002 | Smith | |
| 6,503,726 B2 | 1/2003 | Anne et al. | |
| 6,537,823 B1 * | 3/2003 | Smith | 436/125 |
| 2002/0160439 A1 * | 10/2002 | Anne et al. | 435/25 |
| 2003/0138959 A1 * | 7/2003 | Carter et al. | 436/43 |

OTHER PUBLICATIONS

Mikkelsen, et al., "Adulterants Causing False Negatives in Illicit Drug Testing," *Clinical Chemistry*, vol. 34, No. 11, 1998, pp. 2333-2336.

Warner, Ann, "Interference of Common Household Chemicals in Immunoassay Methods for Drugs of Abuse," *Clinical Chemistry*, vol. 35, No. 4, 1989, pp. 648-651.

Cody, et al., "Impact of Adulterants on RIA Analysis of Urine for Drugs of Abuse," *Journal of Analytical Toxicology*, vol. 13, Sep./Oct. 1989, pp. 277-284.

Bronner, et al., "Detectability of Phencyclidine and 11-nor-$\Delta^9$-Tetrahydrocannabinol-9-Carboxylic Acid in Adulterated Urine by Radioimmunoassay and Fluroescence Polarization Immunoassay," *Journal of Analytical Toxicology*, vol. 14 Nov./Dec. 1990, pp. 368-371.

Schwarzhoff, et al., "The Effects of Adulterating Agents on FPIA Analysis of Urine for Drugs of Abuse," *Journal of Analytical Toxicology*, vol. 17, Jan./Feb. 1993, pp. 14-17.

TSAI, et al., "Determination of Five Abused Drugs in Nitrite-Adulterated Urine by Immunoasays and Gas Chromatography-Mass Spectrometry," *Journal of Analytical Toxicology*, vol. 22, Oct. 1998, pp. 474-480.

Cody, et al., "Effects of Stealth™ Adulterants on Immunoassay Testing for Drugs of Abuse," *Journal of Analytical Toxicology*, vol. 25, Sep. 2001, pp. 466-470.

Wu, et al., "Adulteration of Urine by 'Urine Luck'," *Clinical Chemistry*, Vo. 45, No. 7, 1999, pp. 1051-1057.

Baiker, et al., "Hypochlorite Adulteration of Urine Causing Decreased Concentration of $\Delta^9$-THC-COOH by GC/MS," *Journal of Analytical Toxicology*, vol. 18, Mar./Apr. 1994, pp. 101-103.

Elsohly, et al., "A Procedure to Overcome Interferences Caused by the Adulterant "Klear" in the GC-MS Analysis of 11-nor-$\Delta^9$-THC-9-COOH," *Journal of Analytical Toxicology*, vol. 21, May/Jun. 1997, pp. 240-242.

Paul, et al., "Effects of Oxidizing Adulterants on Detection of 11-Nor-$\Delta^9$-THC-9-Carboxylic Acid in Urine," *Journal of Analytical Toxicology*, vol. 26, Oct. 2002, pp. 460-463.

Department of Health and Human Services, Substance Abuse and Mental Health Services Administration, Center for Substance Abuse Prevention, Division of Workplace Programs, "Guidance for Reporting Specimen Validity Testing," *National Laboratory Certification Program, Program Document 35*, Sep. 28, 1998.

Department of Health and Human Services, Substance Abuse and Mental Health Services Administration, Center for Substance Abuse Prevention, Division of Workplace Programs, "Specimen Validity Testing," *National Laboratory Certification Program, Program Document 37*, Jul. 28, 1999.

Paul, et al., "Effects of Pyridinium Chlorochromate Adulterant (Urine Lock) on Testing Drugs of Abuse and a Method for Quantitative Detection of Chromium (VI) in Urine", *Journal of Analytical Toxicology*, vol. 24, May/Jun. 2000, pp. 233-237.

Singh, et al., The Measurement of Nitrite in Adulterated Urine Samples by High-Performance Ion Chromatography, *Journal of Analytical Toxicology*, vol. 23, May/Jun. 1999, pp. 137-140.

Ferslew, et al., "Capillary Ion Electrophoresis of Endogenous Anions and Anionic Adulterants in Human Urine," *Journal of Forensic Sciences*, vol. 46, No. 3, 2001, pp. 615-626.

Childs, et al., "The Steady-State Kinetics of Peroxidase with 2,2'-Azino-di-(3-ethyl-benzthiazoline-6-sulphonic acid) as Chromogen," *Biochemical Journal*, vol. 145, 1975, pp. 93-103.

Verma, et al., "Excretion of Hydrogen Peroxide in Human Urine," *Free Radic. Res. Commun.*, vol. 8, No. 2, 1990, pp. 73-78 (abstract only).

Kuge, et al., "Relation Between Natriuresis and Urinary Excretion of Hydrogen Perioxide," *Free. Radic. Res.*, vol. 30, 1999, pp. 119-123.

Long, et al., "Hydrogen Peroxide in Human Urine: Implications for Antioxidant Defense and Redox Regulation," *Biochemical and Biophysical Research Communications*, vol. 262, 1999, pp. 605-609.

Cruickshank, et al., "The Presence and Significance of Nitrites in Urine," *The British Medical Journal*, vol. 2, 1914, pp. 712-713.

Smith, et al., "Nitric Oxide Synthase: An Endogenous Source of Elevated Nitrite in Infected Urine," *Kidney International*, vol. 45, 1994, pp. 586-591.

Sasajima, et al., "Changes in Urinary Nitrate and Nitrite During Treatment of Ulcerative Colitis," *Digestion*, vol. 57, 1996, pp. 17-173.

Urry, et al., Nitrite Adulteration of Workplace Urin Drug-Testing Specimens I. Sources and Associated Concentrations of Nitrite in Urine and Distinction Between Natural Sources and Adulteration, *Journal of Analytical Toxicology*, vol. 22, Mar./Apr. 1998, pp. 89-95.

U.S. Environmental Protection Agency, Office of Research and Develoment, "Guidance for Data Quality Assessment, Practical Methods for Data Analysis, EPA/QA/G-9, QA97 Version," *EPA/600/R-96/084*, Jan. 1998.

\* cited by examiner

Figure 1. Absorption spectra of ABTS, DMPDA and APC after oxidized by 3.0 mE/L of ferric ions.

Figure 2. Absorption spectra of XO, HIQSA, and HBSA after complexing with 3.0 mE/L of ferric ions.

DETECTION OF OXIDIZING AGENTS IN URINE

This application claims the benefit of priority under 35 U.S.C. § 119(e) from U.S. Provisional Application Ser. No. 60/479,187, filed Jun. 18, 2003 and U.S. Provisional Application Ser. No. 60/529,700, filed Dec. 16, 2003.

FIELD OF THE INVENTION

The present invention relates to methods and means for detecting oxidants in urine. More specifically, the present invention relates to methods and means for spectroscopic detection of oxidants and oxidizing agents in urine.

BACKGROUND OF THE INVENTION

It is well known in the art that situations arise where it is important to qualitatively or quantitatively determine the presence and concentration of oxidants in a patient's urine. As will be appreciated, accurately detecting the presence of heavy or abnormal concentrations of oxidizing agents in the urine of a patient can help the diagnosis of a patient's condition and appropriate treatment. For example, abnormally high concentrations of oxidizing agents in urine can result from diarrhea in children and other oxidative stress and clinical conditions requiring proper diagnosis and medical attention.

In addition to medical diagnosis, accurately determining, qualitatively or quantitatively, the presence of abnormal concentrations of oxidants in urine is important in other situations. Take drug screening for example. In certain instances and professions, individuals may be required to undergo testing for illegal or banned substances. Although there are very accurate means and methods of determining if an individual has consumed or is under the influence of banned substances, these methods are prohibitively expensive for the random screening of individuals in most instances. Typically, a less-costly alternative is to have an individual provide a urine sample that will be tested for the presence of illegal or banned substances, or more accurately, the metabolites of these substances.

With drug testing, it is customary to perform an inexpensive, initial screening test on a urine sample. If there is a positive result, then the sample can be re-tested with a different method or another sample taken and sent for further testing. This two-step procedure avoids the expense of conclusively evaluating every sample with expensive testing procedures because only the samples that test positive during screening need more rigorous examination for the presence of drugs. Accordingly, individuals who fear that their urine will be positive for the presence of banned substances in the initial test may try to mask the substances or otherwise prevent their detection.

In the past, individuals would try to switch samples or substitute a clean sample for their own. Also, individuals would try to dilute the sample in vitro so that the concentration of the substances resident in the urine would fall below the threshold for detection. These methods of avoiding detection during the testing process are easily prevented by having the individuals monitored while giving a sample (and insuring no water sources are available during the process). Under these conditions, some individuals would try to dilute the sample in vivo. To successfully dilute a sample in vivo, the individual must drink massive quantities of fluids to artificially increase the water content of their urine. To detect and thus prevent this kind of tampering with a sample, urine specimens are routinely analyzed for baseline physiological parameters known to be present in the urine of healthy individuals. For example, specimens are assayed for creatinine concentration and specific gravity, to determine whether the sample has been diluted in vivo.

Adulteration of a urine sample poses unique problems in detecting tampering. "Adulteration" refers to the addition of chemicals to a urine sample to mask the presence of the drug or to interfere with the drug-screening method's ability to detect the drug. A number of readily available commercial products have been used as adulterants. In essence, any product that includes an oxidizing chemical, such as bleach, nitrite, chromate, iodates, or peroxidase, may be effective in preventing a positive reading during the drug screening process. As will be appreciated, some oxidizing agents are effective in destroying 11-nor-delta-9-THC-9-carboxylic acid (THC-acid) and morphine when added to urine samples. Alternatively, these agents can be used to cause conflicting test results by interfering with the immunoassay reagents (as opposed to the drug constituent of the sample) needed to detect the presence of the drugs metabolites.

For example, it has been reported that chromate, nitrite, permanganate, periodate, persulfate, hydrogen peroxide/ferrous ammonium sulfate, and oxone (DuPont product) at a concentration of 10 mmol/L destroy THC-acid almost completely within 48 hours at room temperature. Sodium oxychloride at 50 mmol/L also has similar effects on THC-acid. Moreover, peroxidase from food sources in combination with hydrogen peroxide may effectively destroy THC-acid in a urine sample. Finally, in addition to the masking effect of oxidizing agents, some of these agents also interfere with the GC-MS confirmation procedures typically employed in drug testing, thereby preventing conclusive results.

In an effort to combat adulteration, some prior artisans recommend testing for an adulterant; especially when it appears that a substances is interfering with the drug testing procedures. For example, a procedure for detecting nitrite by diazotizing sulfanilamide and coupling the product with N-(1-naphthyl)ethylenediamine and chromate by 1,5-diphenylcarbazide is in place in many drug-testing laboratories. Alternatively, nitrite can be detected by high-performance ion chromatography and capillary ion electrophoresis. However, both of these procedures suffer from many drawbacks, including exorbitant wastes of time, expense, equipment, and reagents, not to mention the inability of these methods to detect other oxidizing substances.

A qualitative iodide-iodine color test has been proposed for detecting some oxidants. However this test suffers from the severe disadvantage of not having a characteristic absorption spectra in 400-700 nm to permit quantitative analysis.

As will be appreciated, there are countless oxidizing agents that could interfere with the drug-testing procedures or results. Unfortunately, the testing of a urine sample for the presence of each and every oxidant by a procedure unique for each specific oxidant is prohibitively difficult and expensive.

The foregoing underscores some of the problems associated with drug testing. Furthermore, the foregoing highlights the long-felt, yet unresolved need in the art for reliable methods and means for detecting adulterated urine samples. The foregoing also highlights the long-felt, yet unresolved need in the art for reliable methods and means for screening patients to detect abnormal oxidant concentration for diagnosing and treating patients.

SUMMARY OF THE INVENTION

The present invention overcomes the practical problems described above and offers new advantages as well. One object of the invention is to provide a method of detecting oxidants in a biological fluid. It is another object of the invention to provide a method for detecting adulterated urine samples. In accordance with these objects of the invention, an advantageous aspect of the invention is the provision of universal methods, procedures and reagents for detecting the presence of oxidizing agents in urine or the overall oxidant concentration of a sample.

It is another object of the invention to provide methods and means for qualitatively detecting oxidizing agents in a fluid. In accordance with this object of the invention, an aspect of the invention is to qualitatively detect abnormal levels of oxidizing agents in urine. An advantageous feature of the invention is the provision of a screening kit for detecting abnormal levels of oxidizing agents in urine. In one embodiment of the invention, the presence of oxidizing agents is determined by a visible color change or specific hue equated to an impermissible level of oxidizing agents in urine. According to the invention, chromogenic compounds may be used.

It is another object of the invention to provide methods and means for quantitatively detecting oxidizing agents in a fluid. In accordance with this object of the invention, an aspect of the invention is to quantitatively detect the level of oxidizing agents in urine. An advantageous feature of the invention is the provision of a testing system for determining the concentration of oxidizing agent(s) in a sample. In one embodiment of the invention, the quantity or concentration of oxidizing agent(s) is determined by spectrophotometric analysis. According to the invention, chromogenic compounds may be used.

It is another object of the invention to provide compounds and exemplary protocols for detecting oxidizing agents in a fluid. In accordance with this object of the invention, there is provided preferred chromogenic compounds for addition to a sample. According to this object of the invention, one feature of the invention is the detection of oxidizing agents by the chromogenic color of the sample or color change in the sample. Preferably, the chromogenic color of a sample can be compared to the color of a standard(s) having a known oxidant concentration(s). In accordance with one aspect of the invention, the presence of oxidants is determined by initial oxidation of ferrous to ferric ion and detecting the ferric ion by chromogenic oxidation through the addition of chromogenic compounds. According to this aspect of the invention, presently preferred chromogenic compounds include N,N-dimethyamoino-1,4-phenylenediamine (DMPDA); 2,2'-azino-bis(3-ethylbenzthiazoline-6-sulfonic acid) (ABTS); 2-amino-p-cresol (APC); and like compounds. In accordance with another aspect of the invention, the presence of oxidants is determined by initial oxidation of ferrous to ferric ion and detecting the ferric ion by complex formation from the addition of chromogenic compounds. According to this aspect of the invention, presently preferred chromogenic compounds include xylenol orange (XO); 8-hydroxy-7-iodo-5-quinolinesulfonic acid (HIQSA); 4,5-dihydroxy-1,3-benzene-disulfonic acid (HBSA); and like compounds.

In accordance with another object of the invention, there is provided a method of determining adulteration of a urine sample comprising the steps of establishing the oxidizing property of normal urine and urine fortified with oxidizing agents, and determining the presence of oxidizing adulterants from the difference. In one aspect of the invention, the presence of oxidizing agents is determined by spectrophotometry. According to this aspect of the invention, in one embodiment, a standard curve of oxidizing agent concentration is plotted, via spectrophotometric means or otherwise, and a sample is tested for concentration based on its position on the curve. In a preferred embodiment, a sample is spectrophotometrically analyzed and its concentration of oxidants determined by comparison to standards having known concentrations of oxidants. One advantageous feature of the invention is that a statistically significant test for adulteration, preferably Grubbs' test, may be used.

According to another object of the invention, there is provided a method of determining adulteration of a urine sample comprising the steps of contacting a sample with a chromogenic agent and determining if a color is consistent with a statistically significant amount of oxidizing agent being present in the sample. In accordance with this object of the invention, the oxidant concentration of a sample may be determined spectrophotometrically. Alternatively, the oxidant concentration may be determined visually. One advantageous feature of the invention is the ability to test samples in the field with a kit.

In accordance with a presently preferred procedure for detecting oxidants in urine, ferrous ammonium sulfate (FAS) is added to the sample and oxidized by the oxidants to produce ferric ions. According to this procedure, at least one chromogenic compound is added to the sample to allow chromogenic oxidation or chromogenic complex formation. In a preferred embodiment, the color of the sample from chromogenic oxidation or chromogenic complex formation is detected and the concentration of oxidants determined by routine spectrophotometric methods and means, such as running blanks and standards to plot concentration curves for the chromogenic compound(s) and oxidant concentration. In a presently preferred embodiment, chromium VI, or chromate ($Cr^{6+}$), is added to several samples having a known, but different, oxidant concentration to oxidize ferrous ions to ferric ions. Then a chromogenic compound is added for either complex formation or chromogenic oxidation. The known standards are then examined spectrophotometrically at appropriate wavelengths. Urine samples may then be analyzed against the known standards following the procedures described above and the techniques and tools known to those of ordinary skill in the art.

Given the following enabling description and examples, the novel methods, means and compounds of the present invention should become evident to a person of ordinary skill in the art.

BRIEF DESCRIPTION OF THE DRAWINGS

The present invention is described with reference to the accompanying figures.

DETAILED DESCRIPTION

While the present invention is described in connection with testing for adulterated urine in drug testing, it will be readily appreciated by one of ordinary skill in the art that the teachings of the present invention can be applied to a variety of needs in a variety of fields. For example, in cancer patients undergoing radiation therapy, blood peroxide levels may rise.

The present invention provides a method of monitoring peroxide levels to allow suitable adjustment of the radiation levels.

As for use of the present invention with drug testing, typically, to determine if a urine sample has been adulterated, the tester would have to test the sample for the presence of individual oxidizing agents. As will be appreciated, the tester must guess which adulterant was used and thus what to test for. Moreover, if multiple oxidizing agents are suspected or were used, the tester must run individual tests unique for each suspected oxidant to determine its presence or absence in the sample. The difficulty and prohibitive expense of screening for potentially numerous unidentified oxidants is obvious.

The present invention is based, in part, on the discovery that an "oxidizing property" for normal urine can be measured and the overall oxidant concentration in test urine evaluated to discern (qualitatively or quantitatively) if there are abnormal levels of oxidants in the sample. As for the applicability of the present invention in drug testing, the present inventor has devised methods of screening urine to test for statistically significant oxidant concentrations from which a conclusion that the sample has been adulterated can be drawn. Similar to specific gravity and pH, this oxidizing property does not refer or inform as to the actual constituents or oxidants present in urine, but rather refers to the total oxidants in the urine. The upper and lower bounds of this oxidizing property may be calculated according to the invention, and a sample quickly diagnosed as having abnormal or unnatural levels of oxidizing agents.

The present invention is also based on the phenomena of so-called "chromogenic compounds." Chromogenic compounds are precursors of pigments. Typically, these compounds are not themselves a die but capable of forming one under the proper chemical or biological conditions which result in the release of the so-called "chromophore" or "chromogen." These compounds allow a property to be determined if the compound reacts or complexes in an environment to release the "chromophore" or "chromogen" portion of the molecule or otherwise produce a product which results in a change in color, intensity, or absorption at a certain wavelength of the compound or solution which can be discerned visibly or via spectrophotometric or like means. A "chromophore" is best understood as a chemical group (such as an azo group) that absorbs light at a certain frequency so as to impart a discernable color to the molecule. As will be appreciated by one of ordinary skill in the art, "chromogens" or "chromogenic compounds" include a wide variety of substances which may be screened for use in the present invention. Preferred compounds are those that result in a discernable color or intensity change in the presence of an oxidizing agent or ferric ions.

Some preferred means and methods of the present invention are based, in part, on the discovery that the addition of ferrous ions (from the addition of ferrous ammonium sulfate (FAS) or the like) to a sample prior to the addition of chromogenic compound(s) provides unexpected advantages in detecting oxidizing agents otherwise undetectable. The oxidants in the sample convert the ferrous ions to ferric ions and allow numerous other oxidants to be detected via a color change from the addition of chromogenic compounds for complex formation or chromogenic oxidation. For example, the present inventor has discovered that the addition of FAS or a like compound allows for uniform quantitation (mE/L) for oxidizing agents (ferric, nitrite, chromate, permanganate, iodate, periodate, oxichloride, hydroperoxides, persulfate, and oxone). As will be appreciated, characterization and quantitation are the backbones of analytical chemistry. As exemplified with the examples and results below, FAS is particularly suited for used with DMPDA, DEPDA, ABTS, APC, XO, HIQSA, and HBSA. However, FAS appears unsuited for use with 3,3'-dimethylbenzidine (DMBZ) and 3,3',5,5'-tetramethylbenzidine (TMBZ).

In accordance with one embodiment of the invention, chromogenic compounds in water were allowed to react with several oxidizing agents and the absorption intensities of the chromogens were measured at a suitable wavelength to determine the aggregate amount of oxidizing agents.

All oxidizing agents, chromogenic compounds, and vanadium mentioned in the following examples were bought from Sigma-Aldrich Chemicals (Milwaukee, Wis. or St. Louis, Mo.). Solvents and reagents were of analytical or HPLC grade. Negative urine was collected from volunteers and used without preservatives for analysis according to the preferred methods of the present invention. The water was de-ionized before use.

In performing the preferred methods of the present invention, a Spectronic spectrophotometer, model Genesys 2, with a tungsten lamp was used. The cuvettes were made of glass suitable for absorption spectra in the range of 334 to 2500 nm. The optical path and the cell volume were 10 mm and 1.4 mL, respectively. However, as will be appreciated, the present invention may use any suitable spectrophotometric detector and protocol, including those typically used in drug testing.

Chromate, ferric, permanganate, and nitrite reacted well, but periodate, persulfate, hydrogen peroxide, oxone, tert-butyl hydrogen peroxide (TBHP), and cumene hydrogen peroxide (CHP) reacted poorly in the test solution described above. In an alternative and presently preferred embodiment, the oxidizing agents were allowed to react with ferrous ions before any chromogen(s) was added to the test solution. In a preferred process, ferrous ammonium sulfate (FAS) is added to the test solution to allow the oxidants and FAS to react to form ferric ions. The resulting ferric ions are then available to oxidize or to form complex with any one of the various chromogenic compounds suitable for addition to the test solution. The intensity of the chromophore at a suitable wavelength may be evaluated to determine the oxidant concentration or its presence in the sample.

Exemplary reagents, detection methods, and testing protocols are set forth below.

Preparation of Ferrous Ammonium Sulfate (FAS) Solution

A solution of 20 mmol/L FAS was prepared in 0.05M HCl. A few pieces of acid-washed vanadium (~300 mg/100 mL of FAS) were added to the solution to inhibit the oxidation of ferrous to ferric ions. The commercial vanadium was coated with black vanadium trioxide and the soft metal pieces were Vortex-mixed three times with 2 mL of 0.1M HCl (discarding the acid solutions after mixing removed the oxide). The resulting light-gray vanadium was finally washed with water and then used. The FAS solution on vanadium proved stable for at least three months.

Preparation of Oxidizing Agents in Solution

Ferric chloride solutions at appropriate concentrations for use with the present invention were prepared in 10% methanol in water. Solutions of all other oxidizing agents were prepared in water or urine. The persulfate in water solution proved stable for 6 months. All other water solutions were stable for at least two years.

Urine Specimens

A total of 238 specimens in four groups were tested for oxidizing agents by presently preferred methods of the invention. The first three groups of specimens were part of a random drug-testing program and were tested for amphetamines, cocaine, opiates, PCP, and THC before being used in this study. The first group (total 118) tested negative for all drugs. The second group (total 96) was immunoassay positive, but GC-MS negative, for amphetamines. The third group (total 12) was immunoassay and GC-MS positive for THC-acid. The fourth group (8 males and 4 females) was collected from employees of the assignee.

Detection of Oxidants by 2,2'-azino-bis(3-ethylbenzthiazoline-6-sulfonic Acid) Diammonium Salt (ABTS)

A solution of FAS (50 uL, 20 mmol/L in 0.05 M HCl) was added to 50 μL of samples and standards (0, 1.0, and 2.0 mmol/L in water) in separate tubes. Hydrochloric acid (2.5 mL, 0.2 M)) and ABTS solution (2.5 mL, 50 mmol/L in water) were added to the tubes. The pH of the final solution was 1.45. The absorption readings were taken at 415 nm after 5 min of incubation. Water blank was set to zero before sample reading.

Detection of Oxidizing Agents by N,N-dimethylamino-1,4-phenylenediamine. 2HCl (DMPDA)

A solution of FAS (50 uL, 20 mmol/L in 0.05 M HCl) was added to 50 μL of samples and chromate standard (0, 1.0, and 2.0 mmol/L in water) in separate tubes. Hydrochloric acid (1.0 mL, 0.05 M) and DMPDA (1.0 mL, 50 mmol/L in water) were added to the tubes. The pH of the final solution was 1.65. The absorption readings were taken at 553 nm after 7 min of incubation. Water blank was set to zero before sample reading.

Detection of Oxidants by 2-amino-p-cresol (APC)

A solution of FAS (100 uL, 20 mmol/L in 0.05 M HCl) was added to 100 μL of samples and chromate standard (0, 1.0, and 2.0 mmol/L in water) in separate tubes. The color was developed by 1.0 mL of APC (20 mmol/L in 0.1 M HCl). The pH of the final solution was 1.58. The absorption readings were taken at 517 nm after 5 min of incubation. Water blank was set to zero before sample reading.

Detection of Oxidants by Xylenol Orange Sodium Salt (XO)

A solution of FAS (50 uL, 20 mmol/L in 0.05 M HCl) was added to 50 μL of samples and chromate standard (0, 1.0 and 2.0 mmol/L in water) in separate tubes. Hydrochloric acid (5.0 mL, 0.1M)) and XO solution (50 uL, 50 mmol/L in water) were added to the tubes. The pH of the final solution was 1.57. The absorption readings were taken at 560 nm after 5 min of incubation. Water blank was set to zero before sample reading.

Detection of Oxidants by 8-hydroxy-7-iodo-5-quinoline-sulfonic Acid (HIQSA)

A solution of FAS (50 uL, 20 mmol/L in 0.05 M HCl) was added to 50 μL of sample and chromate standard (0, 1.0, and 2.0 mmol/L in water) in separate tubes. A solution of HIQSA (1.0 mL, 2 mmol/L in 0.01 M HCl) was added to the tubes. The pH of the final solution was 2.15. The absorption readings were taken at 610 nm after 5 min of incubation. Water blank was set to zero before sample reading.

Detection of Oxidants by 4,5-dihydroxy-1,3-benzene-di-sulfonic Acid Disodium Salt Monohydrate (HBSA)

A solution of FAS (50 uL, 20 mmol/L) was added to 50 μL of sample and chromate standard (0, 1.0, and 2.0 mmol/L in water) in separate tubes. Hydrochloric acid (1.0 mL, 0.01M)) and HBSA solution (50 uL, 18.7 mmol/L in water) were added to the tubes. The pH of the final solution was 2.13. The absorption readings were taken at 664 nm after 5 min of incubation. Water blank was set to zero before sample reading.

Detection of Oxidants by 3,3'-dimethylbenzidine (DMBZ)

A solution of DMBZ.2HCl (200 uL, 9.43 mmol/L in water) was added to 50 μL of oxidants (0.5 mmol/L in water) and water blank. The solutions were diluted with 1 mL of water. Under this condition the pH was 3.2-3.4 and the color of the solution was blue ($\lambda_{max}$ 635 nm). Proper pH was maintained, otherwise, at pH<1.5 the blue color changed to yellow ($\lambda_{max}$ 440 nm). The absorption readings were taken after 5 min of incubation. Water blank was set to zero before sample reading.

Detection of Oxidants by 3,3',5,5'-tetramethylbenzidine (TMBZ)

A solution of TMBZ.2HCl (50 uL, 20 mmol/L in water) was added to 50 μL of oxidants (1 mmol/L in water) and water blank. The solutions were diluted with 1.5 mL of water and the absorption readings were taken after 5 min using water blank as zero. Under this condition the pH was 3.0-3.2 and the color of the solution was blue ($\lambda_{max}$ 652 nm). Proper pH was maintained, otherwise, at pH<1.5 the blue color changed to yellow ($\lambda_{max}$ 455 nm). The absorption readings were taken after 5 min of incubation. Water blank was set to zero before sample reading.

The foregoing describes exemplary reagents and methods for detecting oxidants in urine as will be elaborated on below. One of ordinary skill in the art will appreciate that numerous other protocols, concentrations and techniques are suitable for use in the present invention. Variations on the foregoing are well within the ability of artisans of ordinary skill without departing from the principles and teaching of the present invention.

In the exemplary methods set forth above, the peracids and hydroperoxides reacted well with the ferrous ions. A number of substituted aminophenols, phenylenediamines, aminonaphthols, and hydroxyquinolines were also tested but only those chromogenic compounds that showed the highest molar absorptivity ($\in$, L.mole$^{-1}$.cm$^{-1}$) are listed in Table I as preferred compounds:

TABLE I

Molar Absorptivity* ($\epsilon$) of Chromogenic Compounds after Ferric Ion Oxidation or Complex Formation.

| Chromogenic Compounds | $\lambda$ nm | $\epsilon$ L · mole$^{-1}$ · cm$^{-1}$ |
|---|---|---|
| ABTS | 415 | 2.304 × 10$^4$ |
| XO | 560 | 1.741 × 10$^4$ |
| DMBZ | 635 | 1.190 × 10$^4$ |
| DMPDA | 553 | 1.046 × 10$^4$ |
| DEPDA | 553 | 9.269 × 10$^3$ |
| TMBZ | 652 | 9.088 × 10$^3$ |
| HIQSA | 610 | 3.535 × 10$^3$ |
| HBSA | 664 | 1.809 × 10$^3$ |
| APC | 517 | 9.267 × 10$^2$ |

*The unit is based on chromogen produced from 1.0 mol/L (or E/L) of ferric ions.

Chromogens, 3,3',5,5'-tetramethylbenzidine (TMBZ), 3,3'-dimethylbenzidine (DMBZ), and N,N-diethylphenylenediamine (DEPDA) were not tested further because the benzidines reacted with FAS; and DEPDA in water was not stable for more than 48 hours. As will be appreciated, one of ordinary skill in the art armed with the present specification can routinely screen compounds through well-known and customary techniques to test any given compound's suitability and desirability for use with the present invention. The present invention should be understood to embrace any compound or reagent that is effective to allow oxidant concentration to be determined visually, spectrophotometrically, or via other comparative means.

As stated above, ferrous solutions were prepared by dissolving ferrous ammonium sulfate (FAS) in 0.05 M hydrochloric acid. The ions in aqueous solution were unstable and continuously changed to ferric ions. A piece of acid-washed vanadium metal (~300 mg/100 mL) stabilized the ferrous solution for at least three months. Similarly, a standard solution of ferric chloride in water was also unstable. However, when dissolved in ≧10% methanol in water, the solutions proved stable for at least two years. Although not wishing to be bound by theory, it is suspected that stabilization may be due to ferric-methanol complex formation.

The reactions of the chromate, ferrous ion, and chromogenic compounds are shown below:

Reactons of Chromate, Ferrous, and Chromogenic Compounds (Chromogenic: ABTS, DMPDA, APC)

(Chromogenic: XO, HIQSA, HBSA)

After the initial ferrous-ferric oxidation, the ferric ions were captured either by chromogenic oxidation (reaction ii) or by chromogenic complex formation (reaction iii). The ferrous ions in reactions i and ii acted as catalysts, but in reactions i and iii they were consumed. Therefore, ferrous ion in excess are preferably used for the complex formation methods, but preferably avoided in the chromogenic oxidation methods. In accordance with reaction (ii) a gradual decrease in absorption with an increasing amount of ferrous ions was observed.

Figure 1:
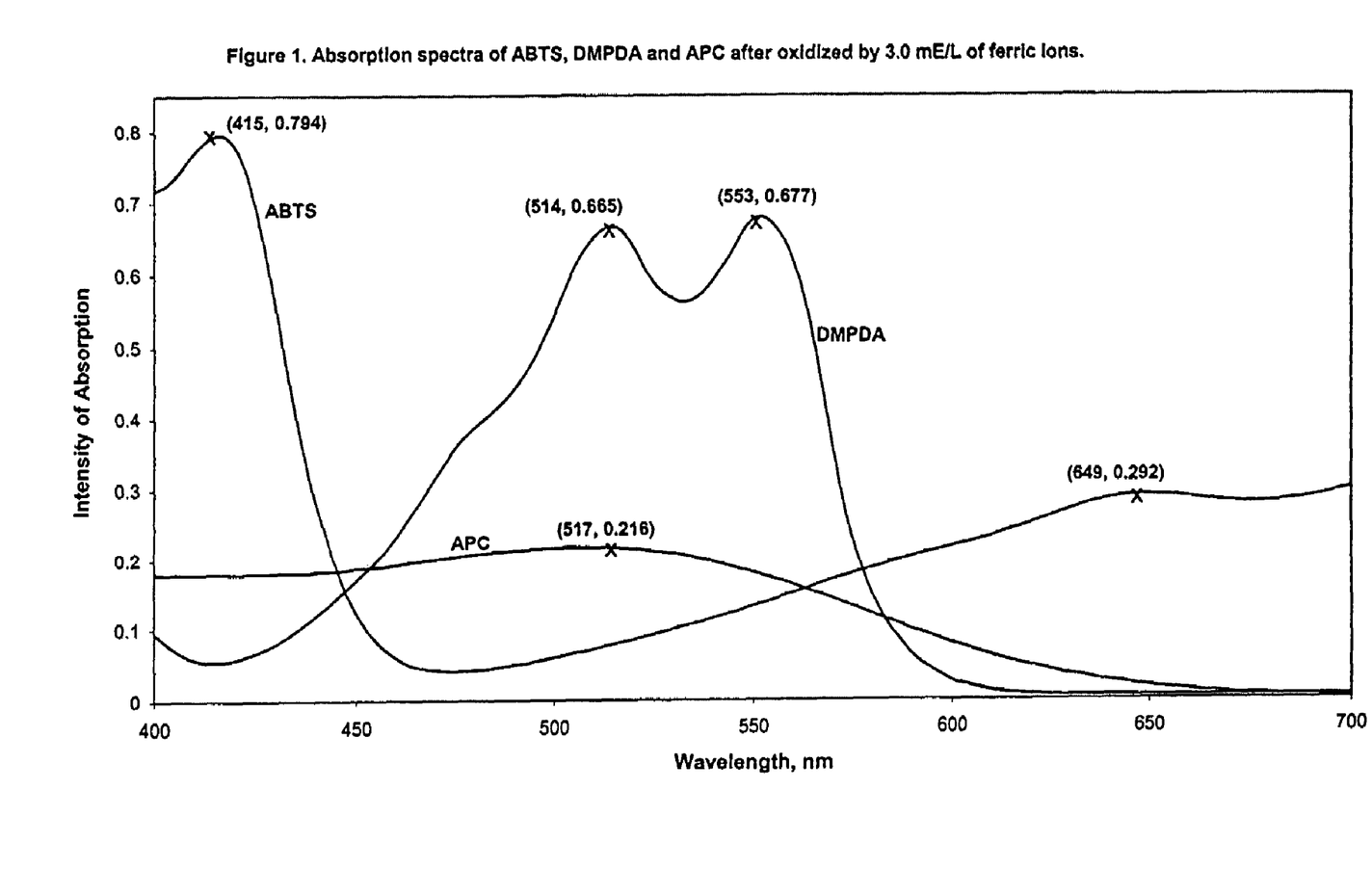
FIG. 1 is an absorption spectra of preferred chromogenic compounds after oxidation with 3.0 mE/L of ferric ions.
Figure 2:
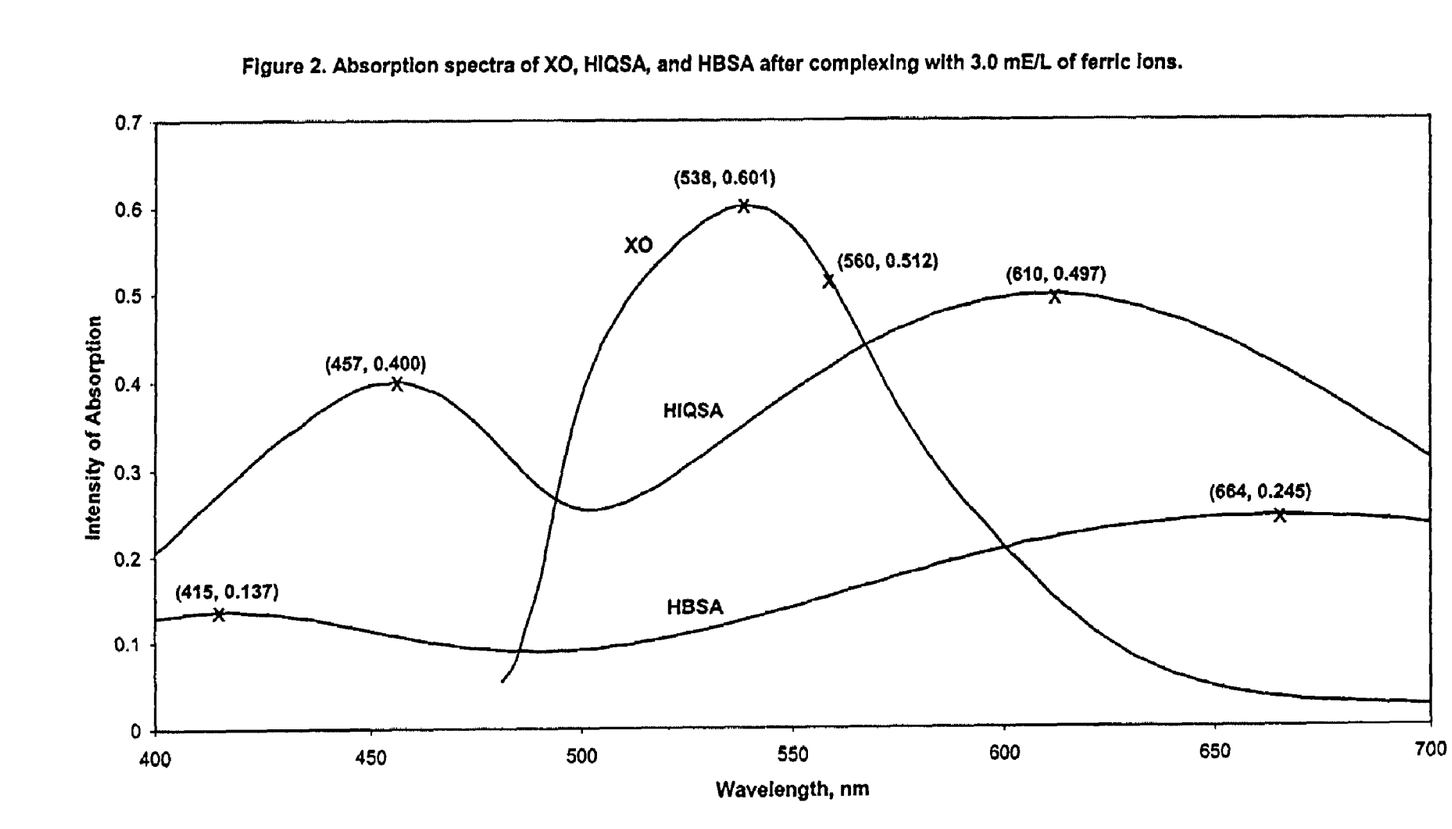
FIG. 2 is an absorption spectra of presently preferred chromogenic compounds after complexing with 3.0 mE/L of ferric ions.

After ferric ion reaction, the absorption spectra of six preferred chromogenic compounds were run. The spectra are shown in FIGS. 1-2. For quantitation, the absorption at the maxima ($\lambda_{max}$) was used for all chromogenic compounds except XO. Absorption at 560 nm on the slope of XO appeared to have less interference by the parent compound than that at $\lambda_{max}$ 538 nm.

The structures of some of the presently preferred chromogenic compounds are not well established. The reactions of DMPDA and ABTS are proposed below:

Oxidation of DMPDA and ABTS to Chromophores

Also, an intermediate radical structure for ABTS has been suggested in the prior art; while the structure of the APC oxidation product is difficult to predict. It could be a 5-position dimer or a compound like Pummerer's ketone. Because the structures of the products are not known, a direct correlation between the molar amount of oxidants and the molar amount of chromogens is not possible. However, the present inventor discovered that the absorption produced by the chromogen appears to be directly proportional to the molar equivalent of oxidant. The quantitative relations between the oxidants tested by six different methods are listed in Table II. The concentrations of the oxidants are expressed in milliequivalent/L (mE/L=mmol/L×Oxidation Number). For 1.0 mmol/L chromate ($Cr^{6+}$) reduced to chromous ($Cr^{3+}$) the value is 3.0 mE/L. Potassium chromate at 99.99% purity was chosen as a standard. Ferric chloride in ≧10% methanol in water was found to be equally suitable. A chromate calibrator at 3.0 mE/L was used to calculate the concentrations of other oxidants. As will be appreciated, one of ordinary skill in the art can devise other suitable standards and calibrators for use in detecting oxidant concentrations according to the invention.

TABLE II

Oxidant Concentrations after One mmol/L of the Oxidants in Water Reacted with Ferrous Ammonium Sulfate and Chromogenic Compounds.

| Oxidants | Theory $E^0$ V | mE/L* | Found by Method, mE/L | | | | | |
|---|---|---|---|---|---|---|---|---|
| | | | ABTS | DMPDA | APC | XO | HIQSA | HBSA |
| Ferric | 0.771 | 1 | 0.91 | 0.88 | 0.93 | 1.00 | 0.98 | 0.98 |
| Nitrite | 0.983 | 1 | 5.12 | 0.58 | 0.68 | 1.52 | 1.70 | 2.10 |
| | 1.297 | 4 | 11.44† | | | 4.35† | 4.62† | 7.60† |
| Chromate‡ | 1.350 | 3 | 3.00 | 3.00 | 3.00 | 3.00 | 3.00 | 3.00 |
| Permanganate | 1.507 | 5 | 4.35 | 4.40 | 4.62 | 4.53 | 4.44 | 4.60 |
| Iodate | 1.085 | 6 | 5.80 | 5.66 | 5.99 | 0.13 | 0.41 | 0.01 |
| | | | | | | 0.61§ | 1.32§ | 0.04§ |
| Periodate | 1.601 | 2 | 7.57 | 7.37 | 7.76 | 1.93 | 2.16 | 1.77 |
| | na | 8 | | | | | | |
| Oxychloride | 1.482 | 2 | 0 | 0.01 | 0 | 0.10 | 0.09 | 0 |
| | | 20‡‡ | 1.05 | 0.97 | 1.03 | 1.35 | 1.39 | 1.34 |
| Hydrogen peroxide | 1.776 | 2 | 1.82 | 1.87 | 1.92 | 1.77 | 1.81 | 1.92 |
| Persulfate | 2.123 | 2 | 1.85 | 1.87 | 1.86 | 1.98 | 1.97 | 1.83 |
| Oxone | na | na | 3.05 | 3.23 | 3.16 | 3.16 | 3.12 | 3.22 |
| TBHP | na | na | 2.39 | 2.64 | 2.40 | 2.57 | 2.57 | 2.78 |
| CHP | na | na | 2.21 | 2.42 | 2.10 | 2.40 | 2.30 | 2.51 |

*mE/L = mmol/L × oxidation number
†Concentrations after 20 min and increasing.
‡Calibrator.
§Concentrations after 20 min.
‡‡Oxychloride at 10 mmol/L or 20 mE/L
na = not available.

All six methods showed comparable results with ferric, permanganate, hydrogen peroxide, persulfate, oxone, TBHP, and CHP (C.V.<7%). The oxidation number of oxone is not known; but from the results it appeared to be 3.16±0.07. The oxidation numbers of TBHP and CHP likewise appeared to be 2.56±0.15 and 2.32±0.15, respectively, compared to 2.0 as the theoretical value. The concentrations of the compounds in the commercial solutions may not be accurate because hydrogen peroxide and other compounds like di-tert-butylperoxide or di-cumene-peroxide may be present in the commercial solutions. The amounts of iodate and periodate were close to the highest oxidation states (6.0 and 8.0 mE/L, respectively) in procedures involving chromogenic oxidation (ABTS, DMPDA, and APC); but the amount of periodate by the chromogenic complex procedures (XO, HIQSA, and HBSA) was close to the lowest oxidation state (2.0 mE/L).

Sodium oxychloride responded weakly; but at a concentration of 10 mmol/L, it showed comparable results between the procedures (1.19±0.19 mE/L). The overall response was approximately 6% of the theoretical amount of 20.0 mE/L. Chlorate and perchlorate did not oxidize the ferrous ions. Activity coefficients (f) for these oxidants may not be enough to initiate the reaction (rate of reaction=rate constant×activity; activity=f×concentration).

No relation was found in the nitrite results. Both oxidation and nitroso substitution on the chromogenic substrates may be the reason for mixed results. Nitroso reactions are common in compounds containing phenolic hydroxyl or amino groups. Gradual increase in absorption with ABTS, XO, HIQSA, and HBSA indicated continued nitroso reaction and oxidation. The absorption readings of nitrite oxidation of DMPDA and APC were stable but the amounts were less than the theoretical amounts (1 or 4 mE/L). The residual amounts of nitrite involved in DMPDA oxidation, however, were linear over the concentration range of 1-10 mmol/L (slope 0.609, intercept −0.030, and R 0.9994).

The linearity, sensitivity, and precision of all six methods are summarized in Table III. Excellent linearity and precision were observed with all methods. Optical saturation was observed at concentrations above the limit of linearity. Some oxidizing agents when dissolved in urine were lost due to reduction. The amount reduced depends on the constituents and pH of the urine, and also on the type of oxidants. Therefore, a chromate standard in urine is unsuitable as the standard. Instead, the chromate standard in water at concentration 3.0 mE/L was used to determine the residual amount of oxidants in urine.

TABLE III

Linearity, Correlation Coefficient (R), Limit of Detection (LOD), and Precision of ABTS, DMPDA, APC, XO, HIQSA, and HBSA Methods for Detection of Chromate in Water.

| Method | Linearity mE/L | Slope | Intercept mE/L | R | LOD mE/L | Precision* Absorption |
|---|---|---|---|---|---|---|
| ABTS | 0.09-12.00 | 0.9597 | 0.0529 | 0.9997 | 0.09 | 0.684 ± 1.7% N = 14 |
| DMPDA | 0.09-12.00 | 1.0006 | 0.0003 | 0.9997 | 0.09 | 0.686 ± 2.7% N = 30 |

TABLE III-continued

Linearity, Correlation Coefficient (R), Limit of Detection (LOD), and Precision of ABTS, DMPDA, APC, XO, HIQSA, and HBSA Methods for Detection of Chromate in Water.

| Method | Linearity mE/L | Slope | Intercept mE/L | R | LOD mE/L | Precision* Absorption |
|---|---|---|---|---|---|---|
| APC | 0.09-12.00 | 1.0010 | −0.0021 | 1.0000 | 0.09 | 0.220 ± 5.6% N = 13 |
| XO | 0.09-6.00 | 0.9865 | 0.0045 | 1.0000 | 0.09 | 0.503 ± 2.4% N = 20 |
| HIQSA | 0.09-6.00 | 0.9334 | 0.0310 | 0.9991 | 0.09 | 0.507 ± 2.6% N = 16 |
| HBSA | 0.09-12.00 | 1.0005 | −0.0015 | 0.9998 | 0.09 | 0.245 ± 1.9% N = 9 |

*Chromate 3.0 mE/L in water from different batch analysis over a period of 6 months.

Stability of 10 mE/L of oxidants in urine stored at −18° C. was studied by the DMPDA method. After preparation, the urine solutions were shaken at room temperature for 1 h and tested (day 0). The solutions were frozen and tested again on day 44. The results are summarized in Table IV. In most cases the loss was on the day of preparation and then fairly stable for at least 44 days. Oxone recovery was only 5.0% on the day of preparation and gradually decreased to a concentration below the limit of detection of the procedure. Strong reduction potentials of permanganate and oxychloride may be the reason of total loss of compound in urine.

TABLE IV

Stability of Oxidants in Urine (10 mE/L) Stored at −18° C. for 44 days and Tested by DMPDA Method.

| Sample in Urine | Recovery, % | |
|---|---|---|
| | Day 0 | Day 44 |
| Ferric | 94 | 88 |
| Chromate | 55 | 40 |
| Nitrite* | 60 | 40 |
| Permanganate | nd | nd |
| Iodate | 74 | 53 |
| Periodate | 51 | 43 |
| Oxychloride | nd | nd |
| Hydrogen peroxide | 31 | 30 |
| Persulfate | 45 | 46 |
| Oxone | 5 | nd |

TABLE IV-continued

Stability of Oxidants in Urine (10 mE/L) Stored at −18° C. for 44 days and Tested by DMPDA Method.

| Sample in Urine | Recovery, % | |
|---|---|---|
| | Day 0 | Day 44 |
| TBHP | 44 | 27 |
| CHP | 56 | 56 |

*Nitrite in mmol/L
nd = not detected

Oxidants dissolved in urine were tested by all six methods (Table V). The relative amounts are comparable with ferric, chromate, hydrogen peroxide, persulfate, oxone, TBHP, and CHP (CV≦11%). Iodate and periodate showed comparable results when tested by chromogenic oxidation procedures. All methods showed positive response for nitrite but the relative amounts varied. The responses were stable with DMPDA and APC methods. With chromogenic complex methods the responses stabilized after 20 min of reaction. With the exception of nitrite, any of the chromogenic oxidation procedures were suitable to characterize the "oxidizing property" of urine. However, every preferred procedure was suitable to establish the presence of oxidizing adulterants in urine, including nitrite. The DMPDA and APC methods are presently preferred because these reagents gave stable readings with all oxidants, including nitrite.

TABLE V

Detection of Oxidants in Urine by Different Methods.

| Oxidant in Urine | Theory ME/L | Found by Method, mE/L | | | | | |
|---|---|---|---|---|---|---|---|
| | | ABTS | DMPDA | APC | XO | HIQSA | HBSA |
| Ferric | 10 | 10.1 | 9.4 | 10.5 | 10.5 | 8.7 | 8.6 |
| Nitrite | 10* | >18 | 6.0 | 4.4 | 11.9 | 12.2 | 17.3 |
| Chromate | 10 | 6.4 | 5.5 | 6.6 | 7.0 | 6.7 | 5.8 |
| Permanganate | 10 | nd | nd | nd | nd | Nd | nd |
| Iodate† | 30 | 21.3 | 22.2 | 22.2 | 1.5 (16.4) | 4.2 (10.7) | nd |
| Periodate† | 10 or 40 | 20.5 | 20.2 | 21.2 | 1.1 (14.8) | 3.5 (9.7) | nd |
| Oxychloride | 10 | nd | nd | nd | nd | Nd | nd |
| Hydrogen Peroxide | 10 | 3.2 | 3.1 | 3.9 | 4.1 | 3.8 | 3.5 |
| Persulfate | 10 | 4.6 | 4.5 | 5.7 | 5.7 | 5.3 | 4.9 |
| Oxone | 10 | 0.5 | 0.5 | 0.6 | 0.6 | 0.6 | 0.5 |

TABLE V-continued

Detection of Oxidants in Urine by Different Methods.

| Oxidant in Urine | Theory ME/L | Found by Method, mE/L | | | | | |
|---|---|---|---|---|---|---|---|
| | | ABTS | DMPDA | APC | XO | HIQSA | HBSA |
| TBHP | 10 | 4.8 | 4.4 | 4.8 | 4.9 | 4.4 | 4.3 |
| CHP | 10 | 6.2 | 5.6 | 5.9 | 6.4 | 5.2 | 5.8 |

*Nitrite in mmol/L
†Results in parentheses were at 20 min.
nd = not detected

The presence of hydrogen peroxide and nitrite in urine has been previously reported in the art. The amount of hydrogen peroxide as tested by XO was reported to be 1.1-112.6 µmol/L (N=10). Notably, lipid hydoperoxides and nitrite interfere with XO under certain conditions. Testing for nitrite by diazo color reaction is relatively specific. The approximate amount after urinary track infection was reported as 3.3 mmol/L.

Figure 3:
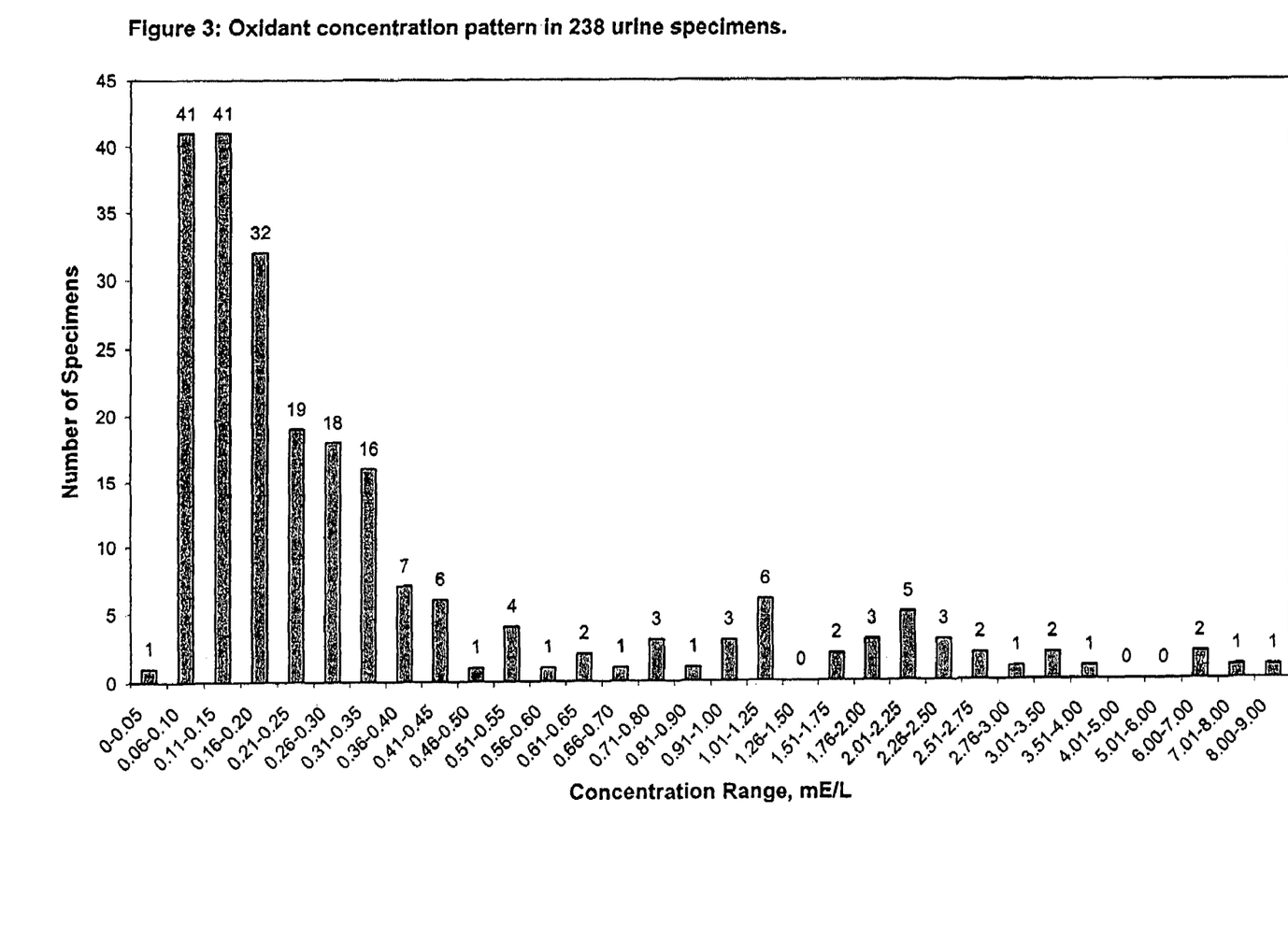
FIG. 3 is a chart plotting the oxidant concentration pattern in 238 urine samples analyzed according to the preferred embodiments of the present invention.

The six methods reported herein were used to find oxidant concentrations in 238 specimens. The specimens were also tested for nitrite by the diazo reaction discussed above. The concentration distributions in the specimens are presented in FIG. 3. Almost 83% (197 out of 238) of the specimens showed oxidant concentration below 1.00 mE/L. The statistical results of 238 specimens are summarized in Table VI.

TABLE VI

Statistical Results of 238 Urine Specimens Tested for Oxidant by Six Methods.

| Total 238 Specimens | DMPDA mE/L | ABTS mE/L | APC mE/L | XO mE/L | HIQSA mE/L | HBSA mE/L | Average† mE/L | Nitrite |
|---|---|---|---|---|---|---|---|---|
| Median | 0.18 | 0.21 | 0.37 | 0.14 | 0.17 | 0.10 | 0.21 | 0.00 |
| Average | 0.59 | 0.71 | 0.72 | 0.58 | 0.66 | 0.46 | 0.62 | 0.05 |
| Standard Deviation | 1.28 | 1.51 | 1.10 | 1.18 | 1.23 | 1.07 | 1.19 | 0.15 |
| Minimum | 0.00 | 0.00 | 0.08 | 0.00 | 0.00 | 0.00 | 0.04 | 0.00 |
| Maximum | 10.32 | 11.42 | 8.36 | 9.14 | 8.25 | 8.33 | 8.83 | 1.21 |
| Slope* | 1.0568 | 1.2256 | 0.8981 | 0.9521 | 1.0006 | 0.8668 | | |
| Intercept* | −0.0674 | −0.0492 | 0.1663 | −0.0119 | 0.0430 | −0.0808 | | |
| Correlation Coefficient* (R) | 0.9853 | 0.9695 | 0.9793 | 0.9600 | 0.9707 | 0.9684 | | |

*Based on the average of six methods
†Average of six methods

The median concentration of the average of six methods was 0.21 mE/L with a range from 0.04 to 8.83 mE/L. The maximum nitrite concentration was 1.21 mmol/L. Only 16 specimens were found to contain nitrite ≥0.10 mmol/L. Regression analysis of the methods resulted in correlation coefficients of 0.9600-0.9853. A higher slope was observed with the ABTS method because some specimens with nitrite responded more with the reagent (slope 1.2256). The methods also showed good correlation in ANOVA test with F=0.90 compared to $F_{critical}$=2.22 at $P_{0.481}$.

To find an extreme value (outlier) that could be related to adulteration, Grubbs' test at 99% confidence level was applied to analyze the values of 238 specimens. In the distribution-plot (not shown), the data appeared to follow a lognormal distribution (Chi-sq=28.027, $Chi-sq_{critical}$=28.845 at $P_{0.025}$ and v=16). The difference between the median and average in the log distribution was smaller than that in the simple distribution. These types of distributions are often found in the EPA environmental data. Specimen 114 with highest oxidant concentration of 8.83 mE/L (Table VII) showed a test value (G=3.128) less than the critical value ($G_{critical}$=4.040 at 99% confidence level, n=238). The result indicated that the specimen is not an outlier. Grubbs' tests were also used to calculate the threshold concentration for an outlier or for a possible adulterated specimen. At the 99% confidence level the calculated concentration is 29 mE/L with G=4.045. After establishing the test criteria, the DMPDA method was applied to a specimen submitted to us for adulterant test. The specimen was found to be positive with oxidant concentration of 1037 mE/L.

Although the Grubbs' test was used in evaluating the present data, one of ordinary skill in the art may utilize alternate statistical tools to devise testing criteria for adulteration and such alternative should be understood as contemplated by the present invention.

With exception of twelve specimens collected from employees of the assignee, the storage conditions of the specimens were not known. Higher concentrations of the oxidants in some specimens may be due to formation of nitrite and hydroperoxides during storage. Other medical conditions may also contribute to the increased amount of nitrite. The results of 35 specimens with oxidant concentration ≥1.0 mE/L are presented in Table VII. Six of the specimens with nitrite concentration >0.50 mmol/L showed relatively higher values with ABTS than with other methods. However, all methods correlated well as judged by the correlation coefficients or ANOVA test.

TABLE VII

Comparative Results of Thirty-five Urine Specimens with Average Oxidant Concentrations ≧1.00 mE/L.

| Specimen Number | DMPDA mE/L | ABTS mE/L | APC mE/L | XO mE/L | HIQSA mE/L | HBSA mE/L | Average† mE/L | Std Dev mE/L | Nitrite mM/L |
|---|---|---|---|---|---|---|---|---|---|
| 13 | 0.84 | 1.18 | 0.95 | 1.14 | 1.22 | 0.85 | 1.03 | 0.17 | 0.32 |
| 46 | 0.99 | 0.77 | 0.84 | 1.16 | 1.69 | 0.75 | 1.03 | 0.36 | 0.17 |
| 138 | 0.91 | 0.99 | 1.14 | 1.01 | 1.37 | 0.88 | 1.05 | 0.18 | 0.00 |
| 171 | 0.93 | 1.98 | 0.56 | 0.74 | 1.53 | 0.59 | 1.05 | 0.57 | 0.57 |
| 31 | 0.82 | 1.01 | 1.31 | 1.37 | 1.11 | 1.02 | 1.11 | 0.20 | 0.00 |
| 51 | 0.85 | 1.04 | 1.67 | 1.13 | 1.28 | 0.96 | 1.16 | 0.29 | 0.01 |
| 105 | 1.15 | 1.22 | 1.54 | 1.04 | 1.40 | 0.99 | 1.22 | 0.21 | 0.00 |
| 103 | 1.46 | 2.00 | 1.36 | 1.45 | 1.94 | 1.22 | 1.57 | 0.32 | 0.31 |
| 176 | 1.36 | 2.09 | 1.68 | 1.15 | 2.50 | 0.68 | 1.58 | 0.66 | 0.57 |
| 185 | 1.34 | 1.56 | 2.10 | 1.40 | 1.91 | 1.22 | 1.59 | 0.35 | 0.01 |
| 98 | 2.11 | 1.38 | 1.63 | 1.67 | 1.84 | 1.90 | 1.76 | 0.25 | 0.06 |
| 9 | 1.42 | 1.68 | 1.65 | 1.80 | 2.34 | 1.93 | 1.80 | 0.31 | 0.01 |
| 119 | 1.61 | 2.16 | 1.36 | 1.79 | 1.97 | 2.07 | 1.83 | 0.30 | 0.00 |
| 59 | 2.29 | 1.81 | 2.01 | 2.12 | 1.95 | 1.90 | 2.01 | 0.17 | 0.00 |
| 61 | 2.00 | 1.91 | 2.26 | 2.01 | 2.20 | 1.70 | 2.01 | 0.20 | 0.00 |
| 182 | 2.12 | 1.88 | 1.49 | 2.53 | 3.23 | 1.55 | 2.13 | 0.66 | 0.01 |
| 55 | 2.18 | 2.15 | 2.29 | 2.07 | 1.99 | 2.22 | 2.15 | 0.11 | 0.07 |
| 113 | 2.22 | 2.61 | 2.65 | 1.70 | 1.90 | 2.20 | 2.21 | 0.38 | 0.01 |
| 62 | 2.52 | 2.55 | 1.91 | 2.62 | 2.18 | 1.85 | 2.27 | 0.34 | 0.00 |
| 56 | 2.55 | 2.27 | 2.21 | 2.70 | 2.57 | 2.42 | 2.45 | 0.19 | 0.24 |
| 170 | 3.04 | 2.14 | 2.72 | 1.89 | 2.45 | 2.65 | 2.48 | 0.42 | 0.02 |
| 52 | 1.78 | 4.26 | 2.05 | 2.24 | 4.16 | 1.51 | 2.67 | 1.22 | 0.82 |
| 42 | 1.19 | 6.40 | 0.97 | 2.17 | 3.54 | 1.78 | 2.67 | 2.04 | 1.21 |
| 85 | 2.29 | 2.68 | 3.47 | 3.23 | 2.51 | 2.18 | 2.73 | 0.52 | 0.00 |
| 77 | 2.85 | 2.75 | 2.63 | 2.96 | 2.74 | 2.54 | 2.75 | 0.15 | 0.01 |
| 49 | 2.48 | 3.24 | 3.08 | 2.82 | 2.84 | 2.88 | 2.89 | 0.26 | 0.01 |
| 111 | 3.29 | 3.63 | 2.94 | 2.14 | 3.37 | 2.83 | 3.03 | 0.53 | 0.18 |
| 130 | 3.16 | 3.13 | 3.23 | 3.03 | 3.72 | 2.15 | 3.07 | 0.51 | 0.00 |
| 155 | 3.76 | 4.51 | 4.62 | 3.60 | 1.87 | 3.25 | 3.60 | 1.00 | 0.01 |
| 108 | 3.11 | 6.87 | 2.96 | 3.51 | 4.76 | 1.95 | 3.86 | 1.73 | 0.92 |
| 128 | 6.79 | 8.53 | 5.48 | 3.88 | 6.55 | 1.89 | 5.52 | 2.35 | 0.68 |
| 18 | 6.18 | 6.54 | 5.62 | 8.34 | 5.92 | 5.70 | 6.38 | 1.02 | 0.00 |
| 110 | 7.95 | 8.46 | 6.69 | 6.06 | 6.55 | 5.95 | 6.94 | 1.03 | 0.23 |
| 39 | 8.17 | 8.64 | 6.69 | 9.14 | 7.22 | 8.05 | 7.99 | 0.90 | 0.00 |
| 114 | 10.32 | 11.42 | 8.36 | 6.31 | 8.25 | 8.33 | 8.83 | 1.79 | 0.03 |
| Median | 2.18 | 2.16 | 2.10 | 2.12 | 2.34 | 1.90 | 2.21 | | |
| Average | 2.80 | 3.36 | 2.69 | 2.68 | 2.99 | 2.36 | 2.81 | | |
| Standard Deviation | 2.31 | 2.67 | 1.85 | 1.97 | 1.84 | 1.87 | 1.98 | | |
| Minimum | 0.82 | 0.77 | 0.56 | 0.74 | 1.11 | 0.59 | 1.03 | | |
| Maximum | 10.32 | 11.42 | 8.36 | 9.14 | 8.25 | 8.33 | 8.83 | | |
| Slope* | 1.1415 | 1.2664 | 0.8995 | 0.9268 | 0.8865 | 0.8792 | | | |
| Intercept* | −0.41 | −0.21 | 0.16 | 0.08 | 0.49 | −0.11 | | | |
| Correlation coefficient, R* | 0.9793 | 0.9409 | 0.9623 | 0.9339 | 0.9532 | 0.9339 | | | |

*Based on average of six methods
†Average of six methods

Effect of storage conditions on specimens was also studied. Fresh specimens from eight male and four female employees were collected and left at room temperature (22° C.) for 18 days. Due to spillage, one specimen was not tested. After collection, the specimens were tested immediately, and again after 11 and 18 days by ABTS, XO, HIQSA, and nitrite methods. ABTS method without FAS was also used to find the hydroperoxide effect. The difference in ABTS results with and without FAS is and indication of hydroperoxide effect. The results are reported in Table VIII.

TABLE VIII

Storage Effect on 11 Fresh Urine Specimens Left at Room Temp for 11 & 18 Days.

| Specimen/ Days at Room Temp | ABTS No FAS mE/L* | ABTS FAS mE/L | XO FAS mE/L | HIQSA FAS mE/L | Average□ mE/L | Nitrite mmol/L |
|---|---|---|---|---|---|---|
| M-1 | 0 | 0 | 0 | 0.03 | 0.01 | 0.00 |
| | 11 | 0.01 | 0.07 | 0.07 | 0.02 | 0.05 | 0.00 |
| | 18 | 1.68 | 1.22 | 0.68 | 0.77 | 0.89 | 0.44 |
| M-2 | 0 | 0 | 0 | 0.06 | 0.05 | 0.04 | 0.00 |
| | 11 | 0.03 | 0.05 | 0.02 | 0 | 0.02 | 0.00 |
| | 18 | 0.23 | 0.19 | 0.31 | 0.33 | 0.28 | 0.15 |
| M-3 | 0 | 0 | 0 | 0.01 | 0 | 0 | 0.00 |
| | 11 | 0.01 | 0.04 | 0.04 | 0 | 0.03 | 0.00 |
| | 18 | 0.02 | 0.08 | 0.11 | 0.06 | 0.08 | 0.00 |
| M-4 | 0 | 0 | 0 | 0.12 | 0.16 | 0.09 | 0.00 |
| | 11 | 0.06 | 0.10 | 0.12 | 0.18 | 0.13 | 0.01 |
| | 18 | 1.42 | 1.18 | 0.86 | 1.00 | 1.01 | 0.43 |
| M-5 | 0 | 0 | 0.01 | 0.27 | 0.40 | 0.23 | 0.00 |
| | 11 | 0.47 | 0.57 | 0.40 | 1.58 | 0.85 | 0.23 |
| | 18 | 2.68 | 7.95 | 8.66 | 4.56 | 7.06 | 0.65 |
| M-6 | 0 | 0 | 0 | 0.14 | 0.17 | 0.10 | 0.00 |
| | 11 | 0.75 | 0.53 | 0.36 | 0.61 | 0.50 | 0.30 |
| | 18 | 0.02 | 3.07 | 3.19 | 2.85 | 3.04 | 0.00 |
| M-7 | 0 | 0 | 0 | 0.27 | 0.45 | 0.24 | 0.00 |
| | 11 | 0.10 | 0.29 | 0.35 | 0.44 | 0.42 | 0.08 |
| | 18 | 2.64 | 11.28 | 10.09 | 7.59 | 9.65 | 0.61 |
| F-1 | 0 | 0 | 0 | 0.06 | 0.06 | 0.04 | 0.00 |
| | 11 | 0.04 | 0.06 | 0.05 | 0.24 | 0.12 | 0.03 |
| | 18 | 0.02 | 0.35 | 0.58 | 0.50 | 0.48 | 0.00 |
| F-2 | 0 | 0 | 0 | 0.06 | 0.04 | 0.03 | 0.00 |
| | 11 | 0.04 | 0.07 | 0.04 | 0.08 | 0.06 | 0.02 |
| | 18 | 0.01 | 3.08 | 2.69 | 2.96 | 2.91 | 0.00 |
| F-3 | 0 | 0 | 0.01 | 0.49 | 0.87 | 0.45 | 0.00 |
| | 11 | 0.06 | 0.59 | 1.98 | 1.61 | 1.39 | 0.01 |
| | 18 | 0.01 | 3.31 | 2.99 | 3.02 | 3.11 | 0.00 |
| F-4 | 0 | 0 | 0 | 0.08 | 0.06 | 0.05 | 0.00 |
| | 11 | 0.05 | 0.04 | 0.02 | 0.13 | 0.06 | 0.01 |
| | 18 | 0.02 | 10.51 | 9.31 | 7.24 | 9.02 | 0.00 |

*Values below 0.10 mE/L may not be accurate.
□Average of ABTS, XO, and HIQSA all with FAS The DMPDA, APC, and HBSA were not used because they were not optimized at the time of experiment. In all cases the total oxidant concentrations increased with increasing time. Seven specimens showed nitrite concentrations ranged between 0.15-0.65 mmol/L. Nitrite in specimen M-6 after 11 days was 0.30 mmol/L. The compound for some unknown reason disappeared after 18 days of incubation. The presence of hydroperoxides was apparent when the results of ABTS with FAS were compared with that of ABTS without FAS. Most specimens showed an increased amount of hydroperoxides after 11 and 18 days of incubation. Hydroperoxide effects are more apparent in specimens with nitrite concentration below 1.0 mmol/L. However, none of the specimens showed oxidant concentrations (highest 11.28 mE/L) more than the threshold concentrations of 29 mE/L.

The volume of specimen used in these methods was 100 μL for APC and 50 μL for all other methods. A higher amount was avoided because it produced defraction. When the oxidant concentration was above the upper limit of linearity, the specimen was diluted with water. Negative urine was avoided because it reduced part of the oxidants in the specimen. The methods are sensitive with the upper limits of quantitation of 6.0-12.0 mE/L. Therefore, dilution is necessary for a specimen to be considered as positive at a cutoff concentration of 29 mE/L. In routine analysis specimens were either tested with 3-5 times dilution, or with the volume of samples reduced to 20-30 μL. During analysis two specimens showed cloudiness in the final solutions. Based on the single wavelength absorption the concentration of the oxidant appeared to be 1.61 and 12.33 mE/L, respectively. On examination of full scan (wavelength 400-700 nm) it appeared that the spectra were considerably different from that of the standard. Defraction from cloudiness may explain the response. When the specimens were centrifuged and the clear solutions were tested again the responses were almost zero. Therefore, it is preferable that after the initial positive result the solution should be tested again under the scan mode to confirm a positive result. Alternatively, the presumptive positive specimens may be centrifuged and tested again under the scan mode. Notably, the different pH of urine appeared to have no effect on the results.

All six methods related well as evident from the statistical data of 238 specimens. The relations were also apparent from test results of urine samples fortified with different oxidizing agents (Table V). The oxidizing property expressed in mE/L is especially useful when specific tests for each oxidizing agent that may be in a sample are not known. Clearly, the present invention saves time and effort when compared to that necessary to test for each oxidizing agent separately.

Generally, oxidizing adulterants in large amounts are used in urine to conceal drug-positive results. As will be apparent from the foregoing disclosure, the three presently preferred chromogenic oxidation methods and the three presently preferred chromogenic complex methods reported herein could be used to detect many commonly available oxidants in urine. These methods and their unexpected advantages overcome many of the shortcomings with prior art techniques. Also, the addition of ferrous ion as taught by the invention may act as an intermediate in the red-ox reaction to improve sensitivity of hydroperoxides and peracids. Although some oxidants after addition to urine were lost due to reduction, the residual amounts were still detected by the preferred methods. In sum, the preferred methods were used to test 238 specimens to establish the oxidant background in urine, or an "oxidizing property" of normal urine. To find an outlier that could be interpreted as adulterated, Grubbs' statistical test was used to analyze the specimen results. None of the specimens was considered as an outlier or as adulterated. Based on the Grubbs' test the threshold concentration for adulteration was calculated as 29 mE/L at a confidence level of 99%. However, one of ordinary skill in the art can choose to use alternative statistical analysis tools and techniques for calculating a suitable threshold value for adulteration or abnormal oxidant levels; and such methods should be understood to be within the scope of the invention.

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

I claim:

1. A method of detecting oxidants in a biological sample comprising:
   adding a source of ferrous ions to said sample, whereby the presence of oxidants in said sample oxidize at least a portion of said ferrous ions to ferric ions;
   adding a chromogenic compound to said sample, whereby said chromogenic compound reacts with at least a portion of any ferric ions present in said sample; and
   detecting for the product of said chromogenic compound-ferric ion reaction;
   whereby the detection of said chromogenic compound-ferric ion reaction product indicates the presence of oxidants in said sample.

2. The method of claim 1 wherein said sample is a biological sample.

3. The method of claim 2 wherein said sample is urine.

4. The method of claim 1 wherein said source of ferrous ions is ferrous ammonium sulfate.

5. The method of claim 1 wherein said oxidants are selected from the group consisting of ferric, chromates, permanganates, iodates, periodates, oxychlorides, hydroperoxides, hydrogen peroxides, persulfates, oxone, tert-butyl hydrogen peroxide, cumene hydrogen peroxide, and nitrites.

6. The method of claim 1 wherein said chromogenic compound-ferric ion reaction product is a chromogen from chromogenic oxidation of said chromogenic compound.

7. The method of claim 6, wherein said chromogenic compound is selected from the group consisting of 2,2'-Azino-bis(3-ethylbenzthiazoline-6-sulfonic acid), N,N-Dimethylphenylenediamine, and 2-Amino-p-cresol.

8. The method of claim 7 wherein said chromogen is detected visually.

9. The method of claim 7 wherein said chromogen is detected via spectrophotometric analysis.

10. The method of claim 4 wherein said ferrous ions are the product of dissolving ferrous ammonium sulfate in hydrochloric acid in the presence of vanadium.

11. The method of claim 1 wherein said chromogenic compound-ferric ion reaction product is a chromogenic complex.

12. The method of claim 11 wherein said chromogenic compound is selected from the group consisting of Xylenol orange, 8-Hydroxy-7-iodo-5-quinolinesulfonic acid, and 4,5-Dihydroxy-1,3-benzene-di-sulfonic acid.

13. The method of claim 12 wherein said chromogenic complex is detected visually.

14. The method of claim 12 wherein said chromogenic complex is detected via spectrophotometric means.

15. The method of claim 12 wherein said ferrous ion is present in excess.

16. The method of claim 1 wherein said detecting step comprises detecting a concentration of said reaction product.

17. The method of claim 16 wherein said concentration is determined by comparing an intensity of said sample to intensities of standards having known concentrations of oxidants.

18. The method of claim 17 wherein said comparison is performed using spectrophotometric means.

19. A method of detecting adulteration of a urine sample comprising:
   adding a source of ferrous ions to a urine sample;
   adding a chromogenic compound to said urine sample;
   detecting the presence or absence of a chromogenic reaction product;
   determining a concentration of said chromogenic reaction product; and
   determining if said concentration signifies adulteration of said urine sample.

20. The method of claim 19 wherein said source of ferrous ions is ferrous ammonium sulfate.

21. The method of claim 19 wherein said chromogenic compound is selected from the group consisting of 2,2'-Azino-bis(3-ethylbenzthiazoline-6-sulfonic acid), N,N-Dimethylphenylenediamine, and 2-Amino-p-cresol, and wherein said chromogenic reaction product is a chromogenic oxidation product.

22. The method of claim 19 wherein said chromogenic compound is selected from the group consisting of Xylenol orange, 8-Hydroxy-7-iodo-5-quinolinesulfonic acid, and 4,5-Dihydroxy-1,3-benzene-di-sulfonic acid, and wherein said chromogenic reaction product is a chromogenic complex.

23. The method of claim 19 wherein said chromogenic reaction product is detected visually.

24. The method of claim 19 wherein said concentration of chromogenic reaction product is determined spectrophotometrically.

25. The method of claim 24 wherein said concentration is determined in milliequivalents per liter of oxidants.

26. The method of claim 25 wherein said milliequivalents per liter is based on comparison of said spectrophotometric results with standards having known milliequivalents per liter.

27. The method of claim 26 wherein said adulteration determination is based on comparison to an oxidizing property of unadulterated urine.

28. The method of claim 27 wherein said sample is determined to be adulterated if the oxidant concentration is determined to exceed 29 milliequivalents per liter.

* * * * *